United States Patent
Grocela

(10) Patent No.: US 7,204,801 B2
(45) Date of Patent: Apr. 17, 2007

(54) PUBOVAGINAL SUPPORT FOR TREATING FEMALE URINARY INCONTINENCE

(75) Inventor: Joseph A. Grocela, Boston, MA (US)

(73) Assignee: Massachusetts General Hospital, Boston, MA (US)

(*) Notice: Subject to any disclaimer, the term of this patent is extended or adjusted under 35 U.S.C. 154(b) by 0 days.

(21) Appl. No.: 10/345,991

(22) Filed: Jan. 17, 2003

(65) Prior Publication Data

US 2004/0143152 A1 Jul. 22, 2004

(51) Int. Cl.
*A61F 2/00* (2006.01)

(52) U.S. Cl. .............................................. 600/30

(58) Field of Classification Search ............ 600/29–31, 600/37; 604/11; 120/885; 128/898, 897; 606/151, 152, 212, 228–231, 157, 158, 213.61, 606/23.72; 623/11–13, 23.64, 23.72, 17.16
See application file for complete search history.

(56) References Cited

U.S. PATENT DOCUMENTS

| | | | |
|---|---|---|---|
| 5,256,133 A | | 10/1993 | Spitz |
| 5,333,624 A | * | 8/1994 | Tovey ......................... 128/897 |
| 5,356,432 A | * | 10/1994 | Rutkow et al. ........... 623/23.72 |
| 5,362,294 A | * | 11/1994 | Seitzinger .................... 600/37 |
| 5,368,859 A | | 11/1994 | Dunn et al. |
| 5,618,256 A | * | 4/1997 | Reimer ......................... 600/29 |
| 5,647,836 A | | 7/1997 | Blake, III et al. |
| 5,716,416 A | * | 2/1998 | Lin ........................... 623/17.16 |
| 5,840,011 A | * | 11/1998 | Landgrebe et al. ............ 600/30 |
| 5,919,233 A | * | 7/1999 | Knopf et al. ................ 128/898 |
| 5,922,026 A | * | 7/1999 | Chin ........................ 623/23.72 |
| 5,934,283 A | | 8/1999 | Willem et al. |
| 6,039,686 A | | 3/2000 | Kovac |
| 6,042,534 A | | 3/2000 | Gellman et al. |
| 6,042,536 A | | 3/2000 | Tihon et al. |
| 6,110,101 A | | 8/2000 | Tihon et al. |
| 6,221,005 B1 | | 4/2001 | Bruckner et al. |
| 6,306,079 B1 | | 10/2001 | Trabucco |
| 6,328,686 B1 | | 12/2001 | Kovac |
| 6,334,446 B1 | | 1/2002 | Beyar |
| 6,382,214 B1 | | 5/2002 | Raz et al. |
| 6,592,515 B2 | * | 7/2003 | Thierfelder et al. ........... 600/37 |
| 6,648,921 B2 | * | 11/2003 | Anderson et al. ......... 623/23.64 |
| 6,652,450 B2 | * | 11/2003 | Neisz et al. ................... 600/30 |
| 2002/0022841 A1 | | 2/2002 | Kovac |
| 2002/0050277 A1 | | 5/2002 | Beyar |

* cited by examiner

*Primary Examiner*—John P. Lacyk
(74) *Attorney, Agent, or Firm*—Reed Smith LLP

(57) ABSTRACT

A device to be surgically inserted for providing bulk and stiffness supporting the urethra. A preferred embodiment is shaped like a capital letter "T." The extensions of the T are wide compared to the patient's anterior vagina and urethra. The pubovaginal support is positioned or implanted under the urethra in the area from mid-urethra to the bladder neck. The body is folded, rolled, or otherwise arranged to provide bulk under the urethra. The pubovaginal support is constructed to be relatively stiff in the area directly supporting the urethra. The extensions retain the device in its position in the vagina without the need for abdominal or pubic bone anchors. The device additionally has some flexibility for easier insertion and comfort while retained in the body. A method of treating incontinence includes inserting the device into pockets dissected in the peri-urethral tissue between the vagina and urethra.

23 Claims, 12 Drawing Sheets

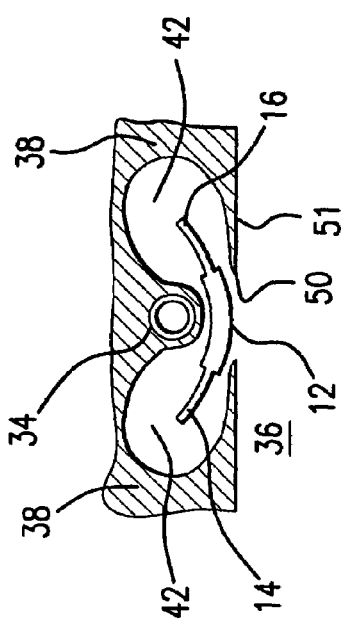
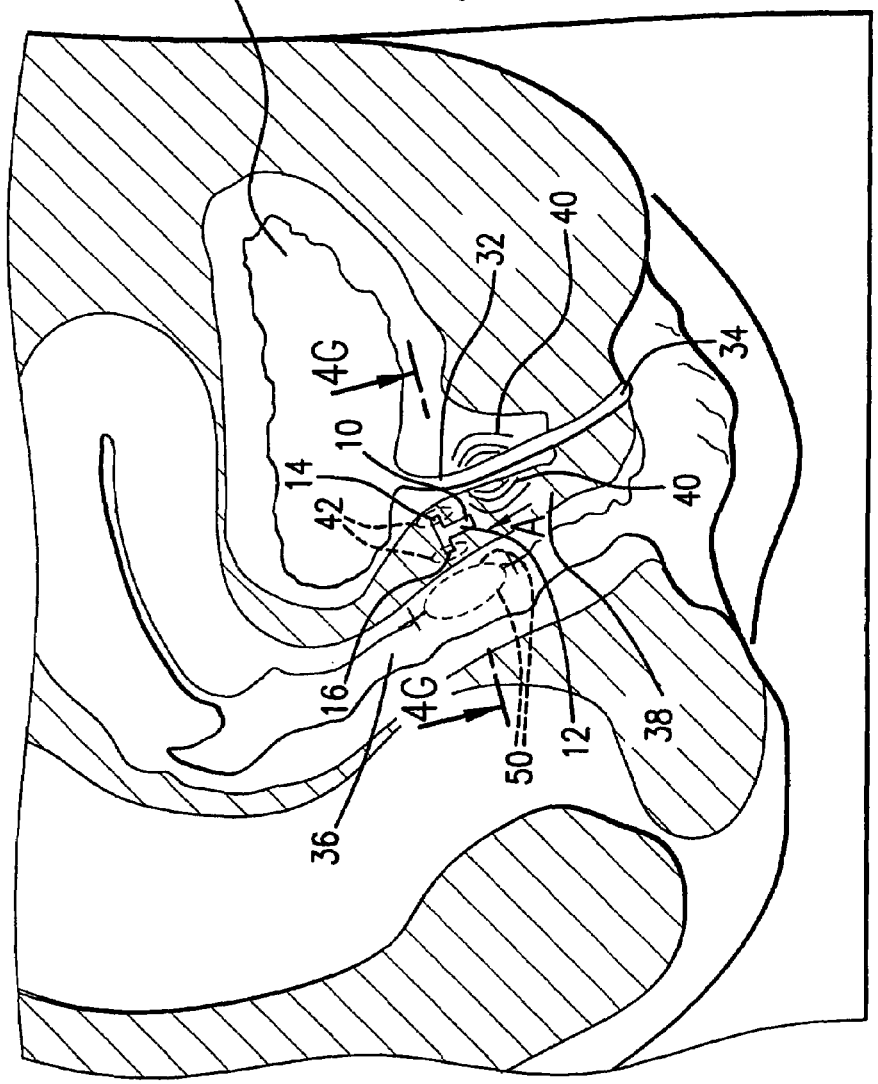

PUBOVAGINAL SUPPORT FOR TREATING FEMALE URINARY INCONTINENCE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates broadly to the problem of female urinary incontinence. More specifically, the invention relates to pubovaginal supports and methods for treating female urinary incontinence.

2. Description of the Related Art

Over 13 million people in the United States experience urinary incontinence. Urinary incontinence is the inability to control the emptying of the urinary bladder. During urination, muscles in the wall of the bladder contract, forcing urine out of the bladder and into the urethra. At the same time, sphincter muscles surrounding the urethra relax, letting urine pass out of the body. Incontinence will occur if bladder muscles suddenly contract or muscles surrounding the urethra are inadequate.

Stress incontinence is a type of urinary incontinence involving involuntary leakage of urine associated with effort, e.g. coughing, laughing, or sneezing. Stress incontinence is often due to weakness of the pelvic floor and bladder outlet. Pelvic floor muscles support your bladder. If these muscles weaken, the bladder drops, pushing slightly out of the bottom of the pelvis toward the vagina. This prevents muscles that ordinarily force the urethra shut from squeezing as tightly as they should. As a result, urine can leak into the urethra during moments of physical stress. Stress incontinence also may occur if the muscles that do the squeezing weaken. Women experience incontinence twice as often as men. Stress incontinence in particular is often caused by the physical changes resulting from pregnancy, childbirth, and menopause. It is the most common form of incontinence in women.

Stress incontinence can be treated by surgical procedures. One method of treating stress incontinence requires surgery to raise the bladder to a more normal position. Working through an incision in the vagina or abdomen, the surgeon raises the bladder and secures it with a string attached to muscle, ligament, or bone. In severe cases of stress incontinence, the surgeon may secure the bladder with a wide sling. This not only holds up the bladder but also compresses the bottom of the bladder and the top of the urethra, further preventing leakage. Slings may further allow for at least partial wrapping of the area to prevent the urethra from opening involuntarily.

Stress incontinence also may be treated by inserting a pubovaginal sling into the pelvis. Pubovaginal slings are physical structures used to support the bladder. Pubovaginal sling implant surgery is performed approximately 100,000 times per year in the United States alone. Current slings require abdominal incisions and use anchors, e.g., staples to implant the sling. Current slings further require anchoring the sling to the patient's pubic bone and/or abdomen, thus requiring multiple incisions, stitching, and the like, throughout the patient's pelvic region. To perform this type of surgery, general or spinal anesthesia often is given to the patient. Further, recovery is prolonged, and the patient's ambulatory functions are reduced during the significant healing time.

Generally, prior devices rely on tension to keep the pubovaginal sling in place. U.S. Pat. No. 6,039,686, issued to Kovac, (the '686 patent) describes a system and method for the long-term treatment of recurrent urinary female incontinence. As illustrated in FIG. 9 of the '686 patent, a sling 29 is anchored using screws 27, 28 in the pubic bone 1a, 1b, and is surgically implanted under the urethra 4. FIG. 10 of the '686 patent illustrates the sling 29 in position and anchored to the pelvis 1.

U.S. Pat. No. 5,647,836, issued to Blake, III et al., (the '836 patent) describes a system and method for treating female urinary incontinence. Anchoring devices or stays 24a,b, are implanted through the vaginal wall 10 and into the muscle or subcutaneous tissue 20, on two opposite sides of the urethra 12. The stays 24a, b, are connected to similar stays 26a, 26b, by sutures 28a, 28b. When drawn tight, the sutures compress the tissues around the urethra.

The pubovaginal sling described in U.S. Pat. No. 5,934,283, issued to Willem et al, (the '283 patent) includes limbs 24, 26, which are surgically implanted in the patient around the abdominal rectus sheath 70.

Although these devices generally functioned well and provided advantages over prior devices, the devices did not provide users with a minimally invasive device implantable without anchors, sutures, and the like. Known devices do not provide a device which can be implanted without typically administering general or spinal anesthesia. Known devices do not provide an implant which does rely on an anchoring mechanism to other bodily structures. Additionally, known devices do not provide a short recovery time.

SUMMARY OF THE INVENTION

According to a first aspect of the present invention, a pubovaginal support useful for treating female urinary incontinence includes a body; and at least two extensions extending away from the body; wherein the body provides bulk and stiffness supporting a bladder neck and a urethra, and the extensions support the body when positioned in surrounding tissue.

According to another aspect of the present invention, a pubovaginal support includes at least two support means for holding the support in at least two pockets dissected in peri-urethreal tissue, and a bulk means for supporting a urethra and a bladder neck.

According to yet another aspect of the present invention, a pubovaginal support includes a body, and at least two extensions extending away from the body, wherein a length of the support measured across the extensions and the body measures approximately 4 centimeters, a thickness of the support measures approximately 0.5 centimeters, and a width of the support measures from approximately 1 to 2 centimeters.

According to yet another aspect of the present invention, a method of treating female urinary incontinence for a patient having a vagina with an anterior wall, a bladder, a bladder neck, a sphincter urethrae muscle, and peri-urethral tissue, includes: making an incision in the anterior wall of the vagina parallel to an area between the bladder and the sphincter urethrae muscle; opening the incision to provide access to the peri-urethral tissue; dissecting at least two pockets in the peri-urethral tissue on either side of a urethra and between the bladder and sphincter urethrae muscle; positioning a pubovaginal support, including a body and at least two extensions, underneath the urethra and the bladder neck and between the bladder and the sphincter urethrae muscle, with the at least two extensions placed in the at least two pockets; and closing the incision.

Additional aspects and advantages of the invention will be set forth in part in the description which follows and in part will be obvious from the description, or may be learned by practice of the invention.

BRIEF DESCRIPTION OF THE DRAWINGS

The accompanying drawings, which are incorporated in and constitute a part of this specification illustrate some embodiments of the invention and, together with the description, serve to explain the advantages and principles of the invention. In the drawings.

FIGS. 4a–4i illustrate a method of implanting an exemplary pubovaginal support of the present invention using an exemplary method in accordance with the present invention.

DETAILED DESCRIPTION OF THE PREFERRED EMBODIMENTS

The present invention has been made in view of the deficiencies in the prior art, described above. One aspect of the present invention is to provide an anchorless pubovaginal support for urinary incontinence. Another aspect of the invention is to provide a pubovaginal support that is implantable without making abdominal incisions. Another aspect of the present invention is to provide a pubovaginal support implantable while administering a minimal amount of local anesthesia. Yet another aspect of the present invention is to provide an incontinence implant that does not create or cause tension on other bodily structures. Still another aspect of the present invention is allowing for rapid recovery from a pubovaginal support implant procedure.

The pubovaginal support of the present invention includes a device for providing bulk and stiffness supporting the urethra. According to a preferred embodiment, the device is shaped like a capital letter "T." The extensions of the T are wide compared to the patient's anterior vagina and urethra. The pubovaginal support is positioned or implanted under the urethra, in the area from mid-urethra to the bladder neck. The body of the "T" is folded, rolled, or otherwise arranged, to provide bulk under the urethra.

The pubovaginal support is constructed to be relatively stiff in the area directly supporting the urethra. The extensions retain the device in its position in the peri-urethral tissue without the need for abdominal or pubic bone anchors. The device additionally has some flexibility for easier insertion and comfort while retained in the body. Alternative embodiments, which do not include a folded, rolled or otherwise arranged portion of the body, do include material with increased bulk and stiffness in the body area adjacent to the urethra and bladder neck. A method of treating incontinence includes inserting the device into pockets dissected in the peri-urethral tissue between the vagina and urethra.

Figure 1B:
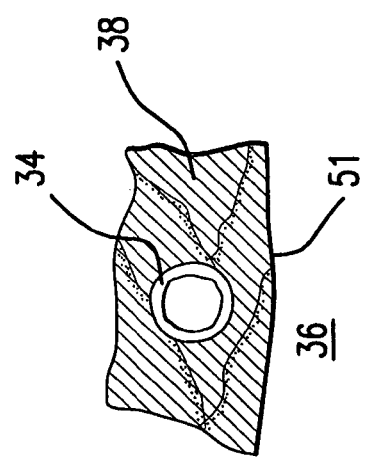
FIG. 1b illustrates the location of human organs and anatomical structures relevant to the present invention, in a superior sectional view of the female pelvic region.
Figure 1A:
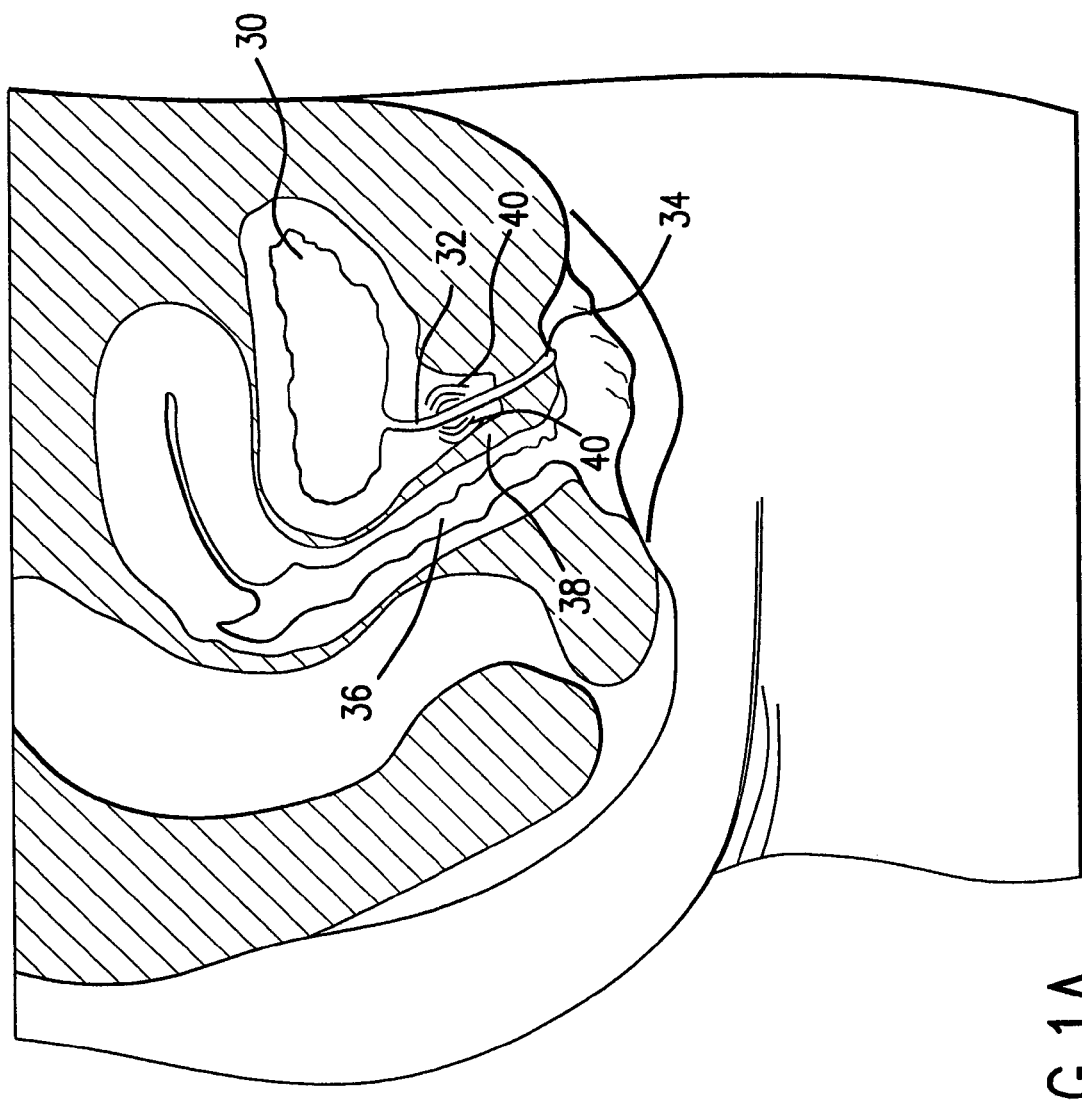
FIG. 1a illustrates the location of human organs and anatomical structures relevant to the present invention, in a midsagittal sectional view of the female pelvic region.

The present invention will be better understood by first describing the anatomical structures involved when treating female urinary incontinence. FIGS. 1a and 1b illustrate the location of human organs and anatomical structures relevant to the present invention, in a midsagittal sectional view, and superior sectional view, respectively, of the female pelvic region. A bladder 30 tapers to a bladder neck 32. The urethra 34 extends generally inferiorly, i.e., towards the feet, away from the bladder neck 32. The sphincter urethrae muscle 40 surrounds the urethra 34 below the bladder neck 32. The vagina 36, with anterior wall 51, lies posteriorly from the urethra 34. The peri-urethral tissue 38 is a connective tissue in the pelvic area, found between the vagina 36, bladder 30, and bladder neck 32, and sphincter urethrae muscle 40.

Figure 2:
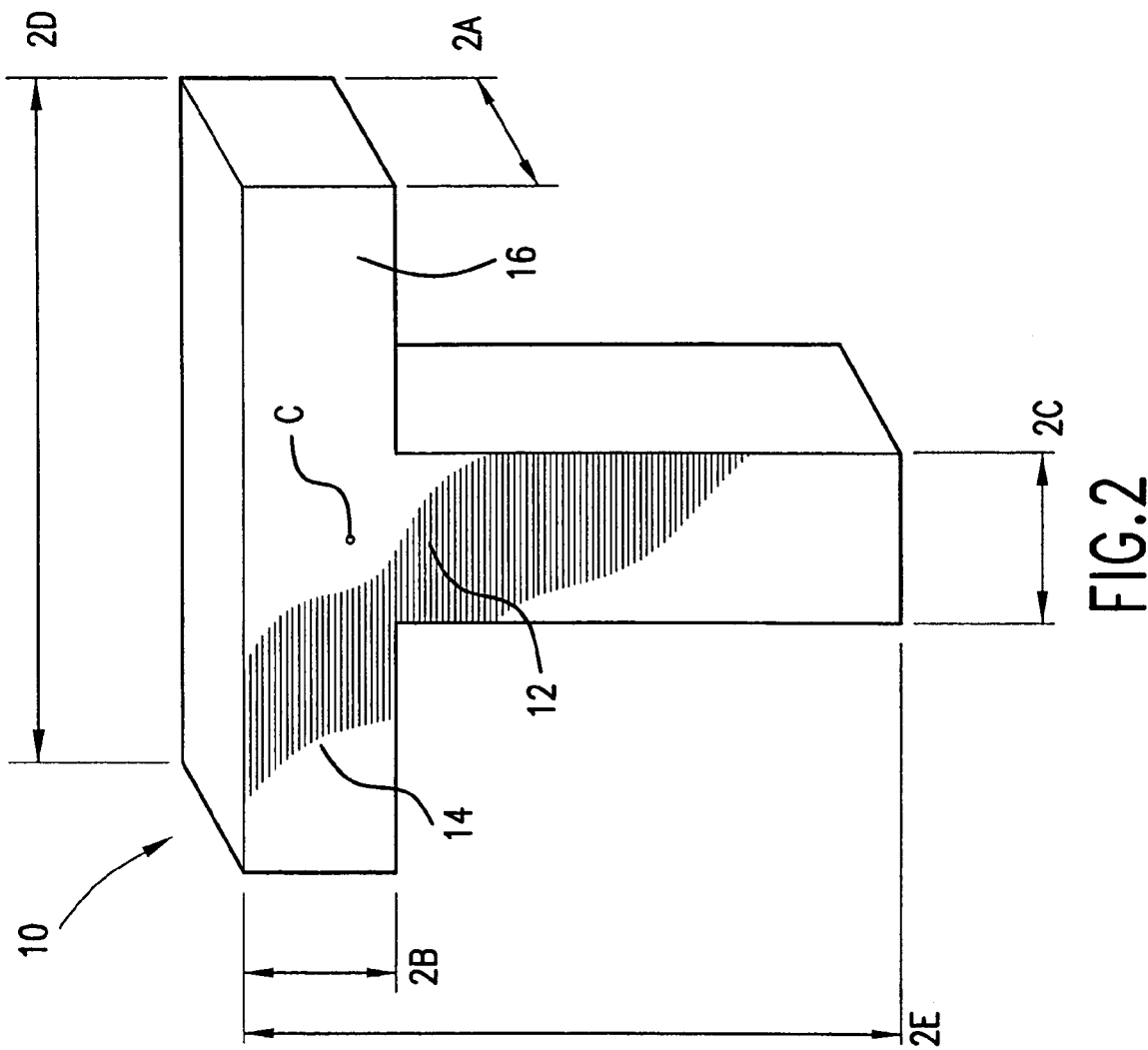
FIG. 2 illustrates a first exemplary embodiment of a pubovaginal support in accordance with the present invention.

FIG. 2 illustrates a first exemplary embodiment of a pubovaginal support 10 in accordance with the present invention. The pubovaginal support 10 is preferably shaped like a capital letter "T", with a body 12 and two extensions 14, 16, generally perpendicular to the body 12. The extensions 14, 16 support the support 10 when it is implanted into tissue and also bear stress from the bladder. The body 12 can be rolled, folded, or otherwise arranged toward the extensions to place added bulk and stiffness under the urethra 34, as further described below.

The support 10 is dimensioned to be wider than a patient's urethra 34. The thickness of the support 10 is selected so that when implanted adjacent to the urethra 34, the support 10 exerts pressure against the urethra 34. According to a preferred embodiment, the body 12 provides a balance between the wider dimension, which may provider, more support, and smaller dimension, which may be easier to install. The length of the body 12 is selected to be approximately the same as the length of the urethra 34 between the bladder neck 32 and sphincter urethrae muscle 40, which is about 1 to 3 centimeters.

According to a preferred embodiment, the thickness of the support 10, along line 2A, measures approximately from 2 millimeters to 1 centimeter, and more preferably, the thickness of the support measures about 0.5 centimeters. The width of the support 10, along line 2B, preferably measures 0.5 to 3 centimeters, and more preferably from 1 to 2 centimeters. The length of the body 12 of the support 10, along line 2C, preferably measures from 0.5 to 3 centimeters. The length of the support 10 across the extensions and the body, along line 2D, preferably ranges from 2–5 centimeters, and more preferably, has a length of approximately 4 centimeters. The height of the body, along line 2E, preferably measures from 1–6 centimeters.

The support 10 has material properties of both rigidity and flexibility. The rigidity supports the bladder and urethra without collapsing the urethra. Rigidity may be uniform throughout, or apportioned more to the portions of the device which, when implanted as described herein, are adjacent to the urethra and bladder neck. Additionally, where stiffness properties of the material are increased, less bulk is required. Preferably, the support 10 has stiffness and bulk such that the support 10 deflects 0 to 3 millimeters, preferably 2 to 3 millimeters, under 500 grams of weight applied at a center, C, of the support 10. Alternatively, however, the support 10 may be fabricated of a material with very little intrinsic stiffness, but including increased bulk up to one additional centimeter.

Another aspect of the present invention is that the pubovaginal support 10 is made from a biocompatible material with slight stiffness properties. The rigidity provides strength to absorb downward pressure exerted by the bladder and to stay secured in place by slightly pressing against the walls of the vagina. Yet, the material is sufficiently flexible to bend and be manipulated during insertion. Preferably, the support 10 is made from a bioabsorbable material, and more preferably, collagen. Cross-linking mesh, e.g., Dacron, may be added for increased stiffness. Other suitable bioabsorbable materials include Polydiaxonone Suture (PDS) or Vicryl. Bioabsorbable materials are preferred because they allow the body to form organic structure over time to support the bladder neck and urethra. However, biocompatible nonabsorbable materials may be used without departing from the scope of the present invention. Suitable biocompatible materials include, but are not limited to, surgical stainless steel, nitinol, polypropylene (e.g., Prolene), and nylon.

Figure 3A:
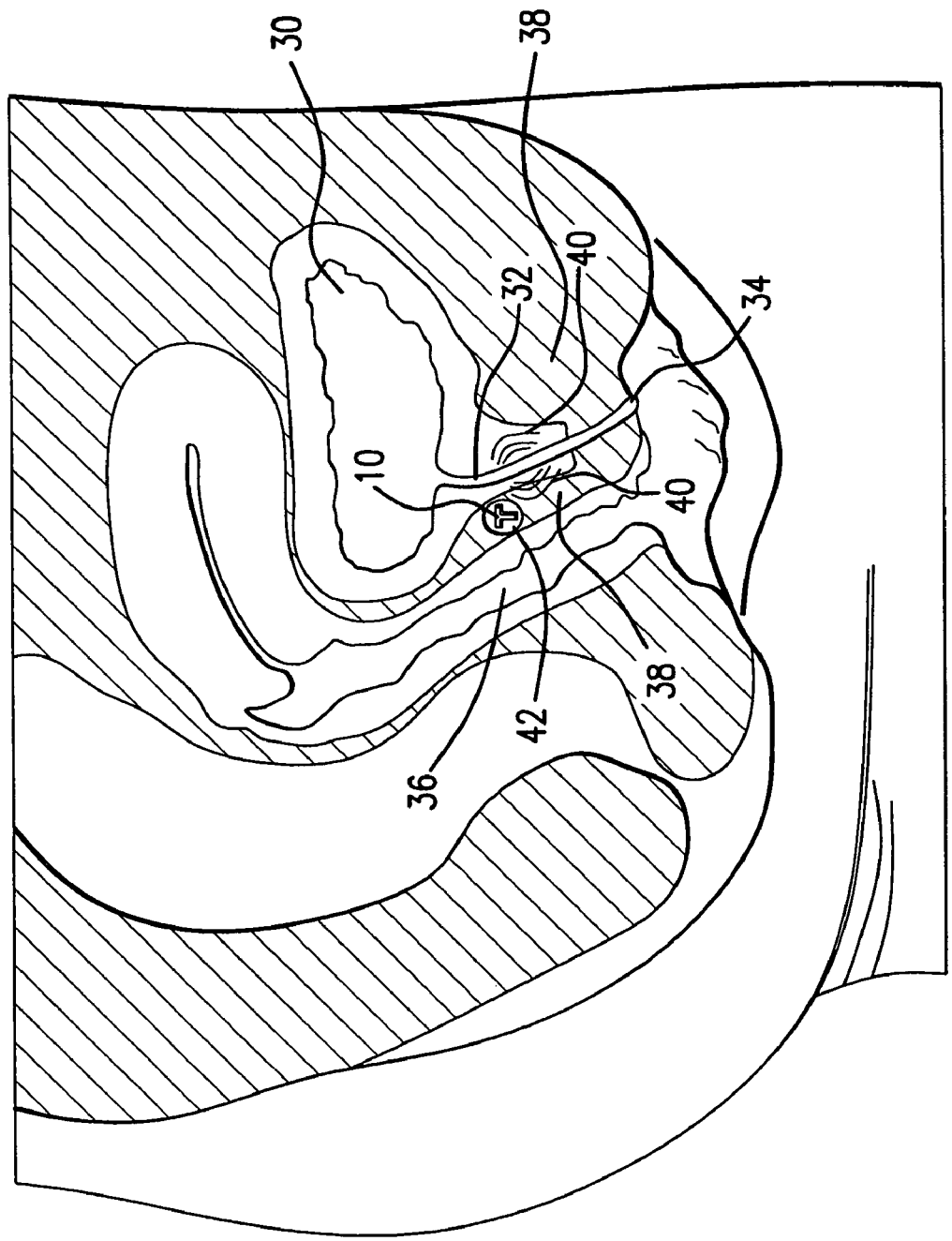
FIG. 3a illustrates a midsagittal sectional view of the female pelvic region with a pubovaginal support implanted in accordance with the present invention.
Figure 3B:
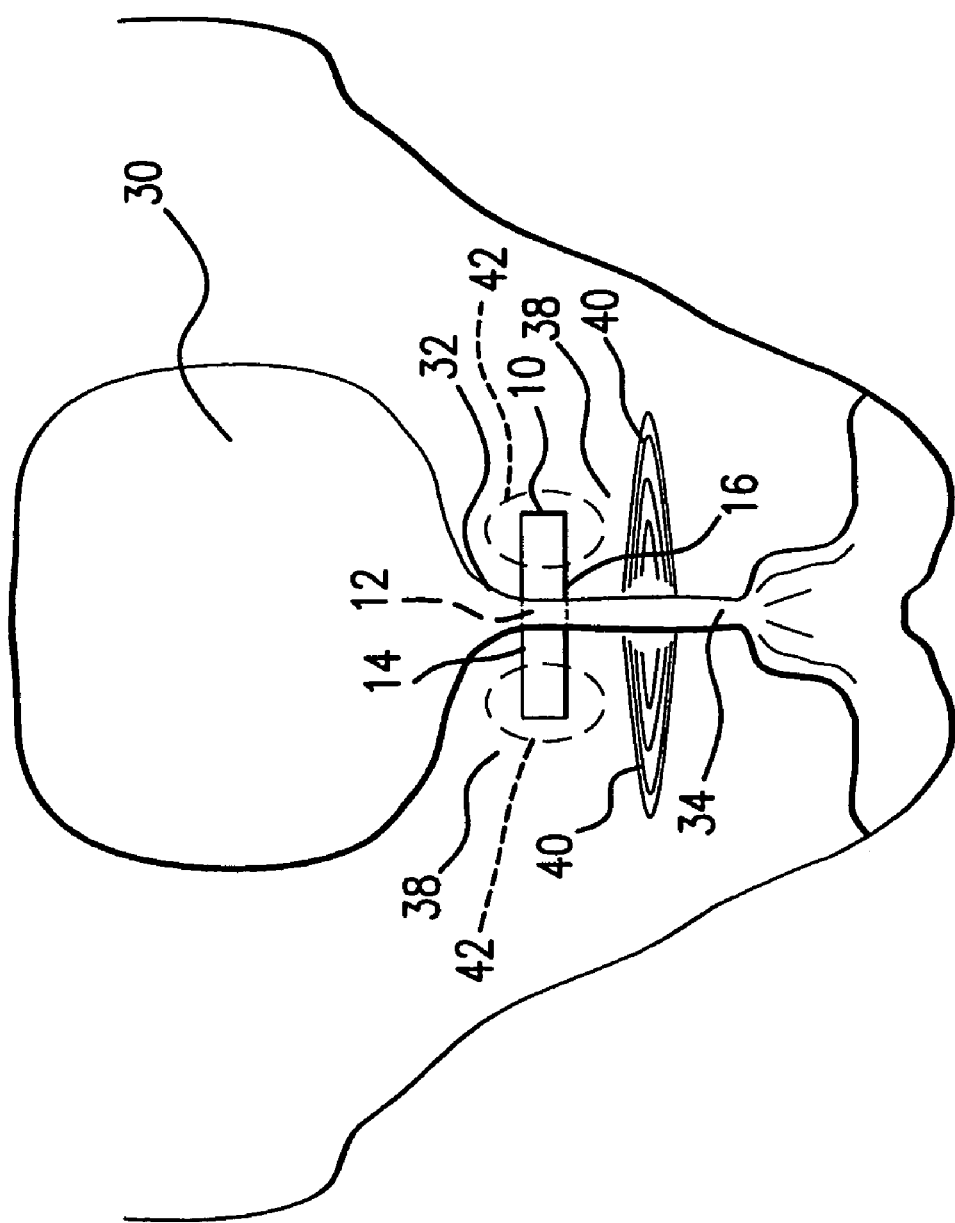
FIG. 3b illustrates a female frontal sectional view with a pubovaginal support implanted in accordance with the present invention.

FIGS. 3a and 3b illustrate the support 10 of the present invention inserted within the body, in a midsagittal sectional view and frontal sectional view, respectively, of the female pelvic area. The support 10 is placed in the patient within pockets 42 cut into the peri-urethral tissue 38, located anterior to the vagina 36 and posterior to the urethra 34. The body 12 of the support 10 is disposed along the length of the urethra 34. The thickest portion of the support 10 is placed in the area between the bladder neck 32 and the sphincter urethrae muscle 40, adjacent to the urethra 34. On average, the distance between the bladder 30 and the sphincter urethrae muscle 40 ranges from 1 to 3 centimeters. With the preferred embodiment, the body 12 of the support 10 can then be rolled, folded or otherwise arranged, to provide further bulk supporting the bladder neck 32 and urethra 34, and bearing weight from the bladder 30.

Figure 4B:
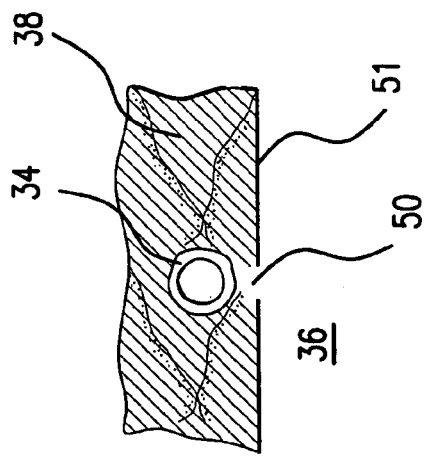
Figure 4A:
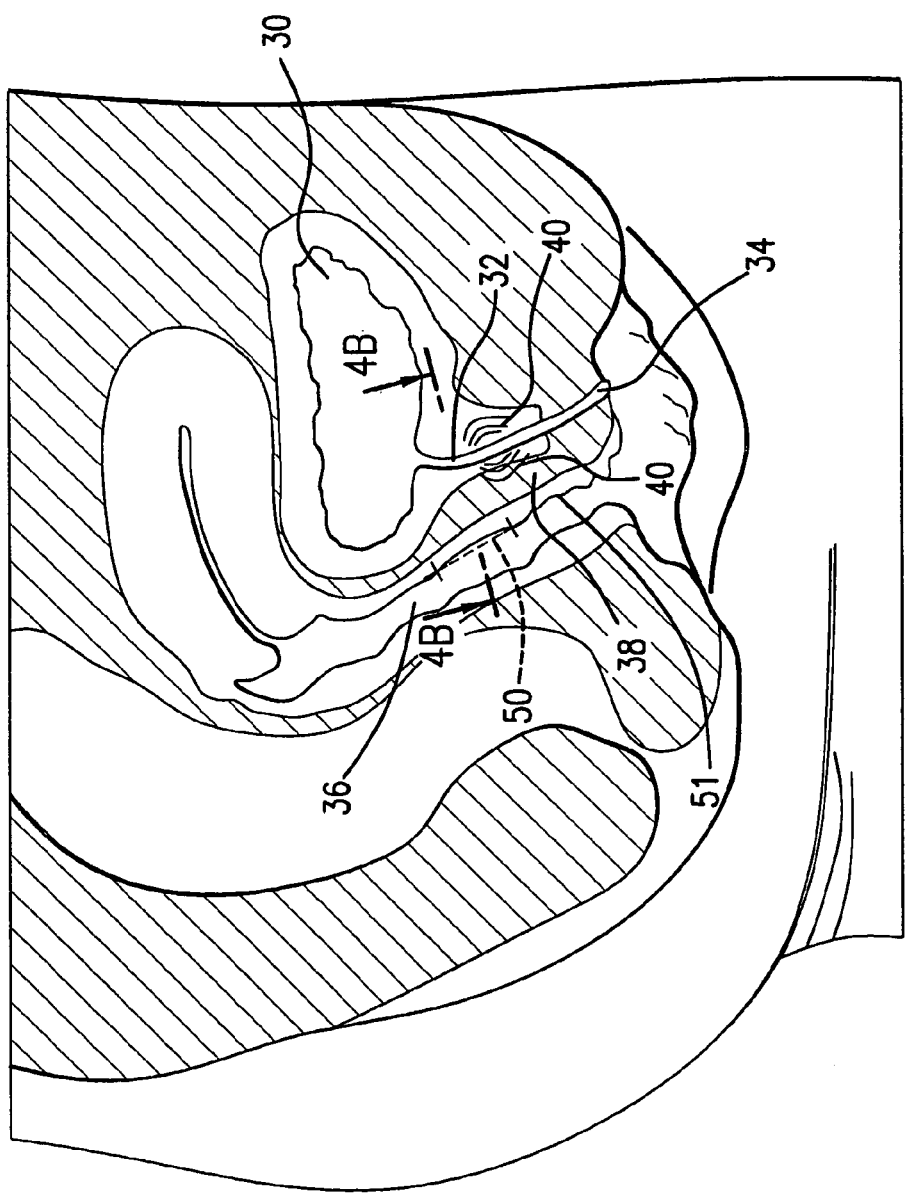
Figure 4C:
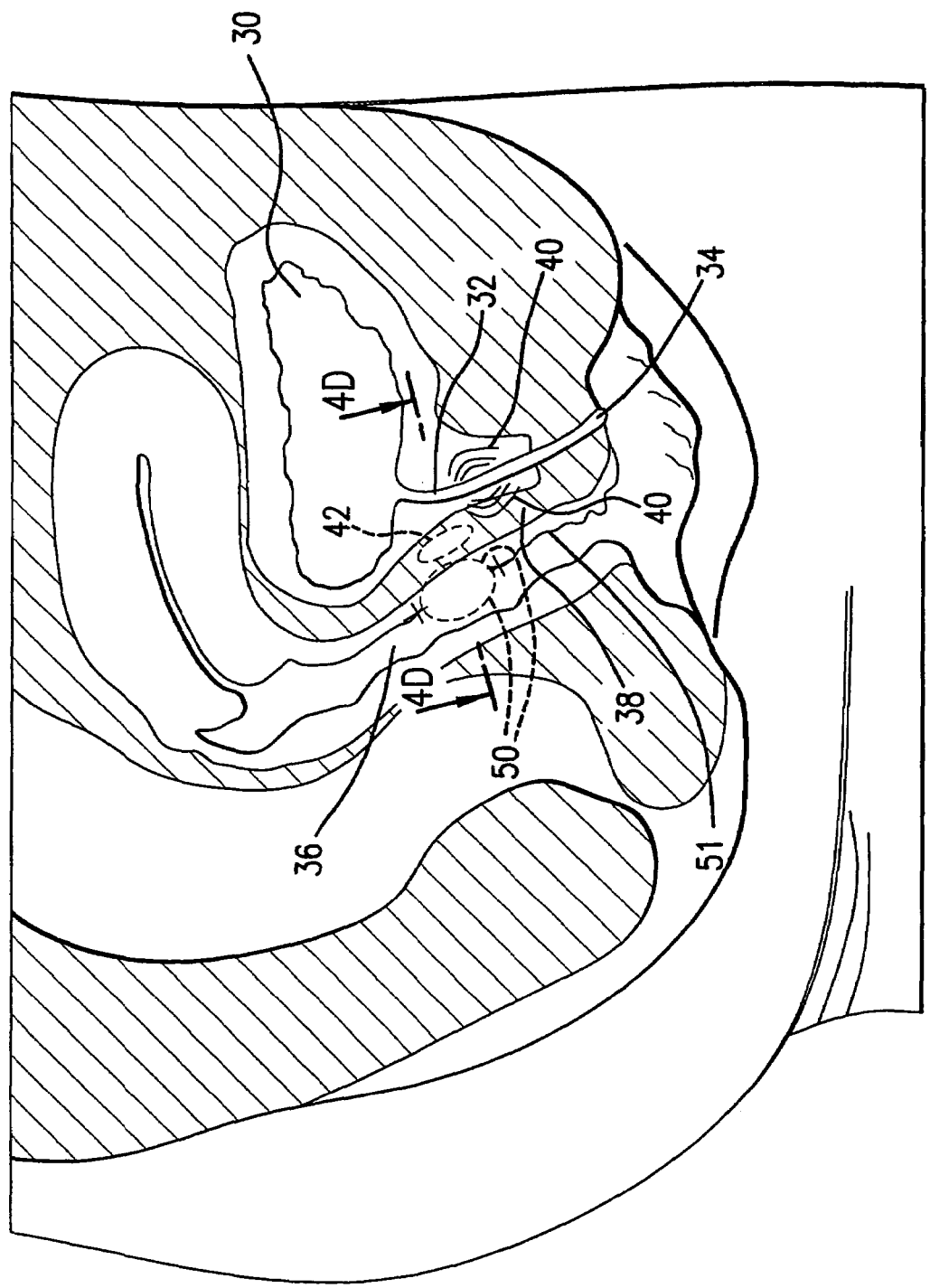
Figure 4D:
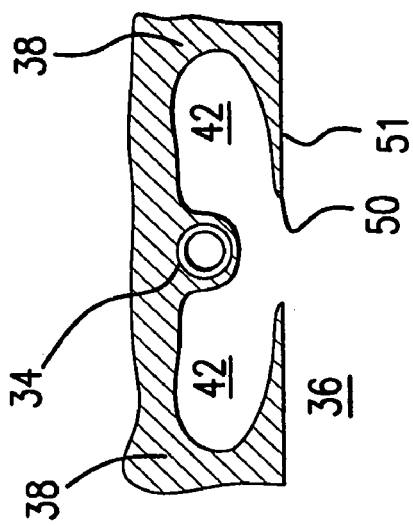
Figure 4E:
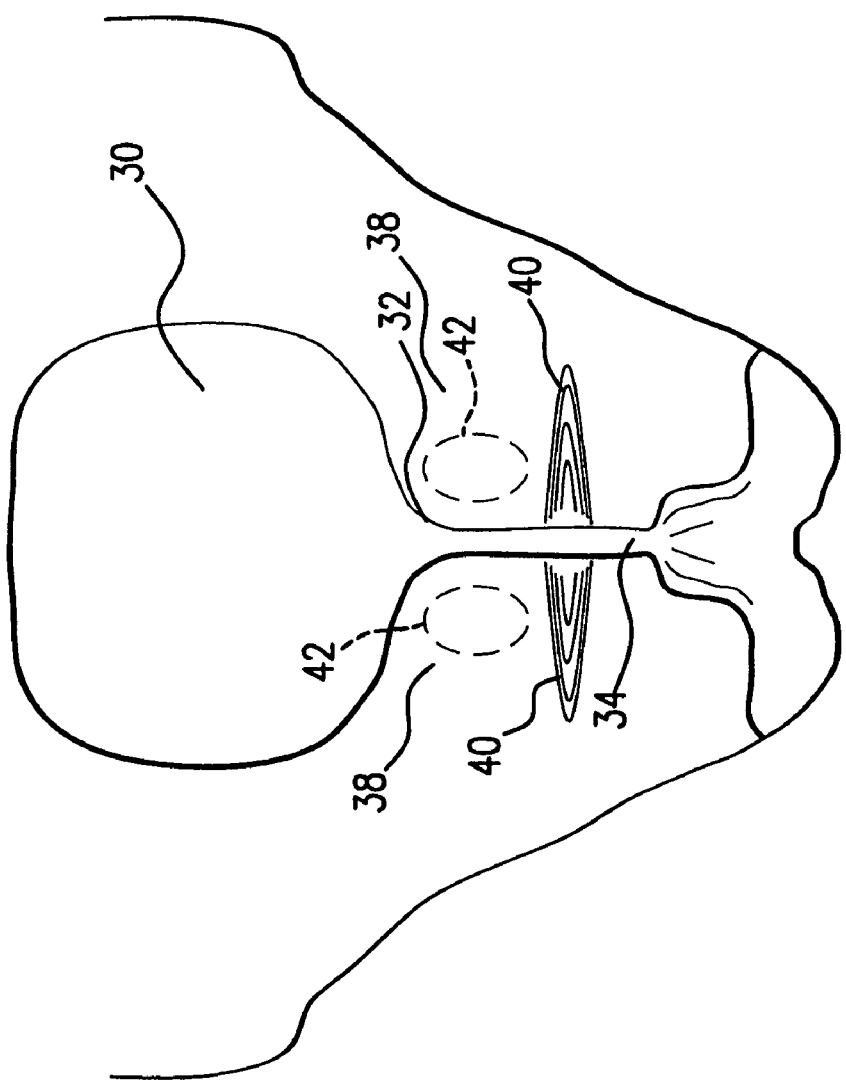
Figure 4H:
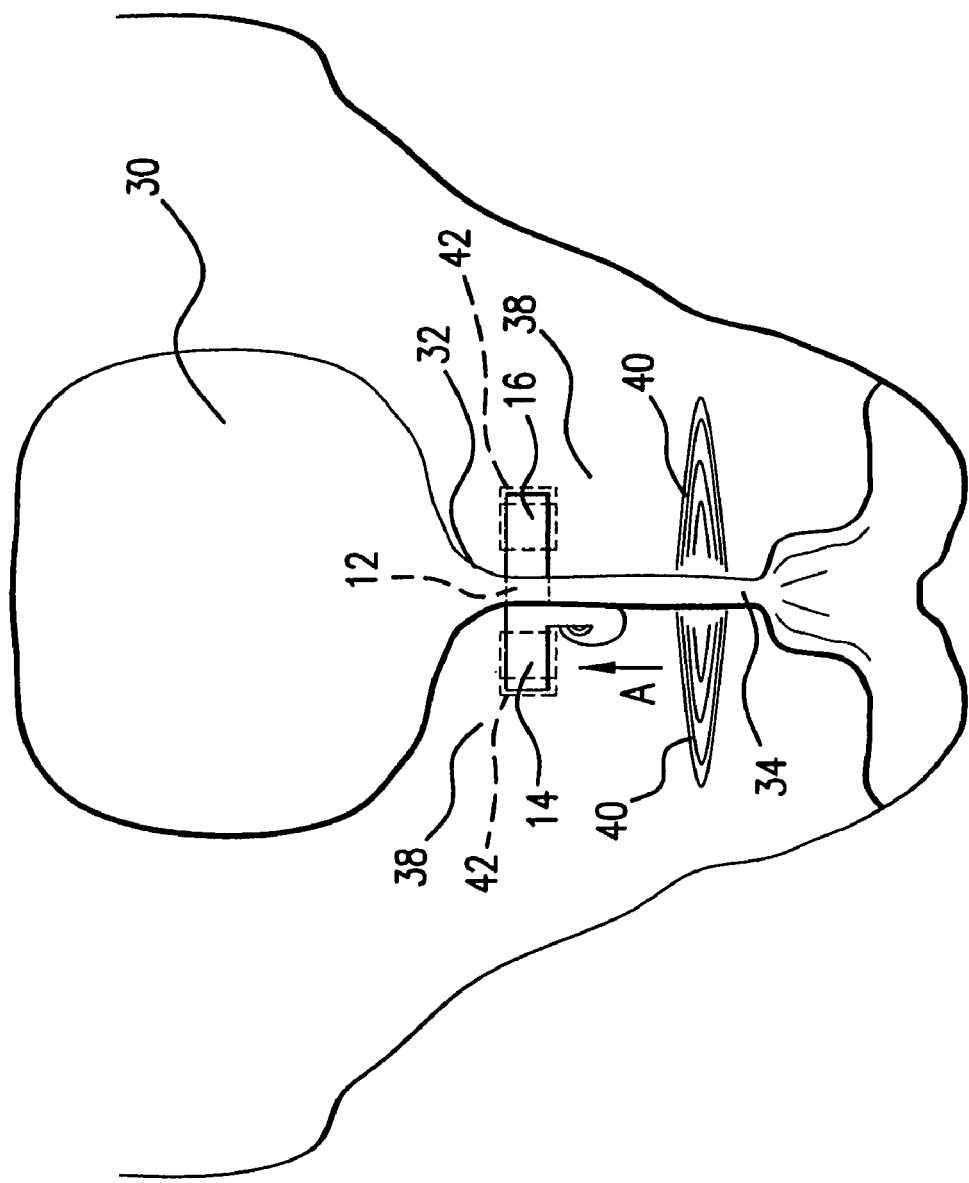
Figure 41:
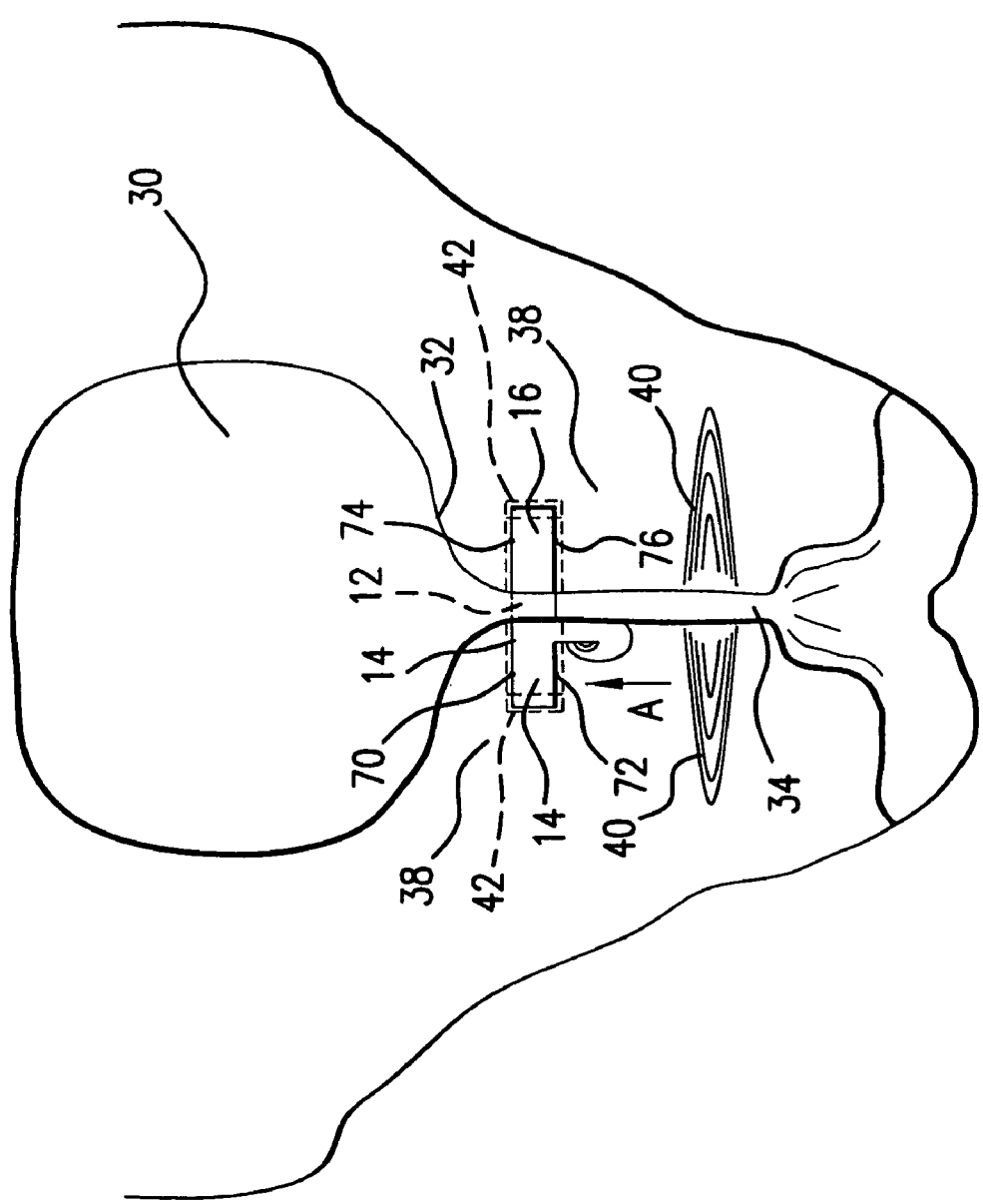

FIGS. 4a through 4i illustrate an exemplary method of implanting a pubovaginal support of the present invention. FIGS. 4a, 4c, 4f, illustrate a midsagittal sectional view of the female pelvic area. FIGS. 4b, 4d, and 4g illustrate a superior sectional view of the female pelvic area. FIGS. 4e, 4h, and 4i illustrate a frontal sectional view of the female pelvic area.

Referring to FIGS. 4a and 4b, an incision 50 is made along an anterior wall 51 of the vagina 36, from in to out, generally parallel to the urethra 34. Optionally, a probe, e.g., ultrasonic probe, may be placed within the urethra to help identify both the proper incision point and placement of the support 10. A probe inserted into the urethra 34 may fit up to the bladder neck 32. The physician can lightly tap the anterior vaginal wall to feel the probe's location. Since the area from the top of bladder neck 32 down towards the sphincter urethrae muscle 40 ranges, on average, from 1 to 3 centimeters, the physician feels the top of the probe, measures about 3 centimeters down towards the sphincter urethrae muscle 40, and places the incision 50 in between.

Referring to FIGS. 4c–4e, once the incision 50 is made, the incision 50 is dilated or opened to provide access to the peri-urethral tissue 38, located anterior to the vagina 36 and posterior to the urethra 34. Next, two pockets 42 are dissected, from medial to lateral, into the peri-urethral tissue 38. The pockets 42 are positioned on either side of the urethra 34.

Next, referring to FIGS. 4f and 4g, the support 10 is implanted within the patient. FIG. 4f illustrates the cross-sectional view at a plane angled relative to that of FIGS. 4a and 4b, so that both pockets 42 can be illustrated with portions 14, 16 of the support 10 inserted therein. Optionally, the support 10 may be rolled, folded, or otherwise arranged prior to being placed in the body to make passage through the incision and into the peri-urethral tissue 38 less difficult. It is shown not folded in FIG. 4f. The support 10 is placed along the posterior side of the urethra 34 between the bladder 30 and the sphincter urethrae muscle 40. The portion of the support 10 having the most bulk and stiffness is placed below the bladder neck 32 and urethra 34.

The embodiment of support 10 has a body 12 that may be rolled, folded, or otherwise arranged, as shown by FIG. 4h, to provide added bulk.

The present invention relates to the field of pubovaginal slings but is not intended to require the use of sutures or other means for securing the device within the patient. The support 10 may be kept in place simply by the extensions 14, 16, sitting within the pockets 42. Optionally, however, the support 10 may be additionally secured using sutures or surgical glue. Further optionally, the extensions 14, 16 may include materials, such as Dacron, to promote tissue ingrowth to further stabilize the device in situ.

FIG. 4i illustrates suture points used with the preferred, T-shaped embodiment of the present invention, if needed. Preferably four suture points 70, 72, 74, 76, are used, with two points on each extension 14, 16. However, other numbers of sutures, more or less, may be used. The procedure ends by closing the vaginal incision 50.

Alternatively, the stitches used to close the vaginal incision may be looped through the support 10 to hold it in place until natural tissue in-growth begins. Due to the minimal amount of incision and dissection needed to implant the support 10, the procedure may be performed using only a local anesthetic. Since no abdominal incisions are needed, the patient's recovery time is significantly decreased and less painful when compared to other implant procedures. Additionally, less tissue dissection helps to minimize the patient's risk of developing infection.

Figure 5A:
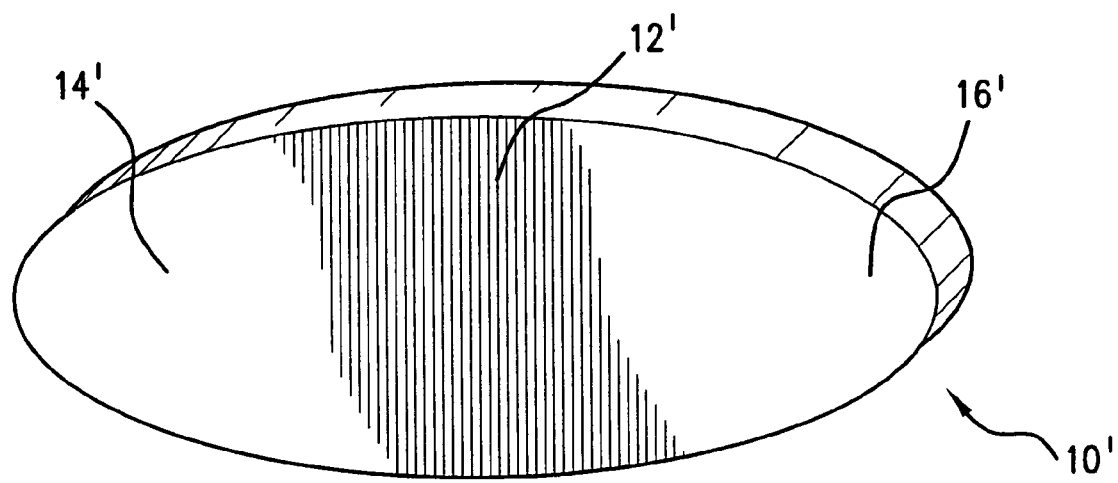
FIGS. 5a–5c illustrate alternative embodiments of pubovaginal supports in accordance with the present invention.
Figure 5B:
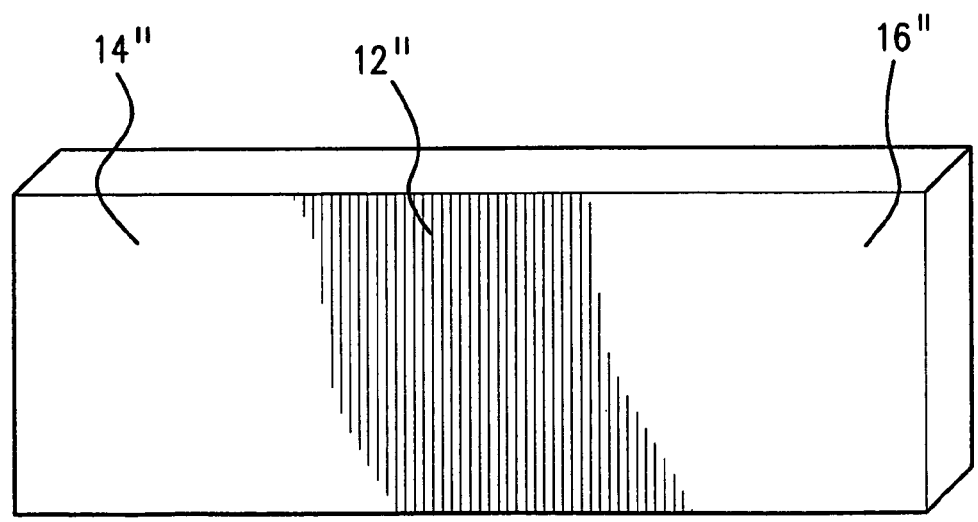
Figure 5C:
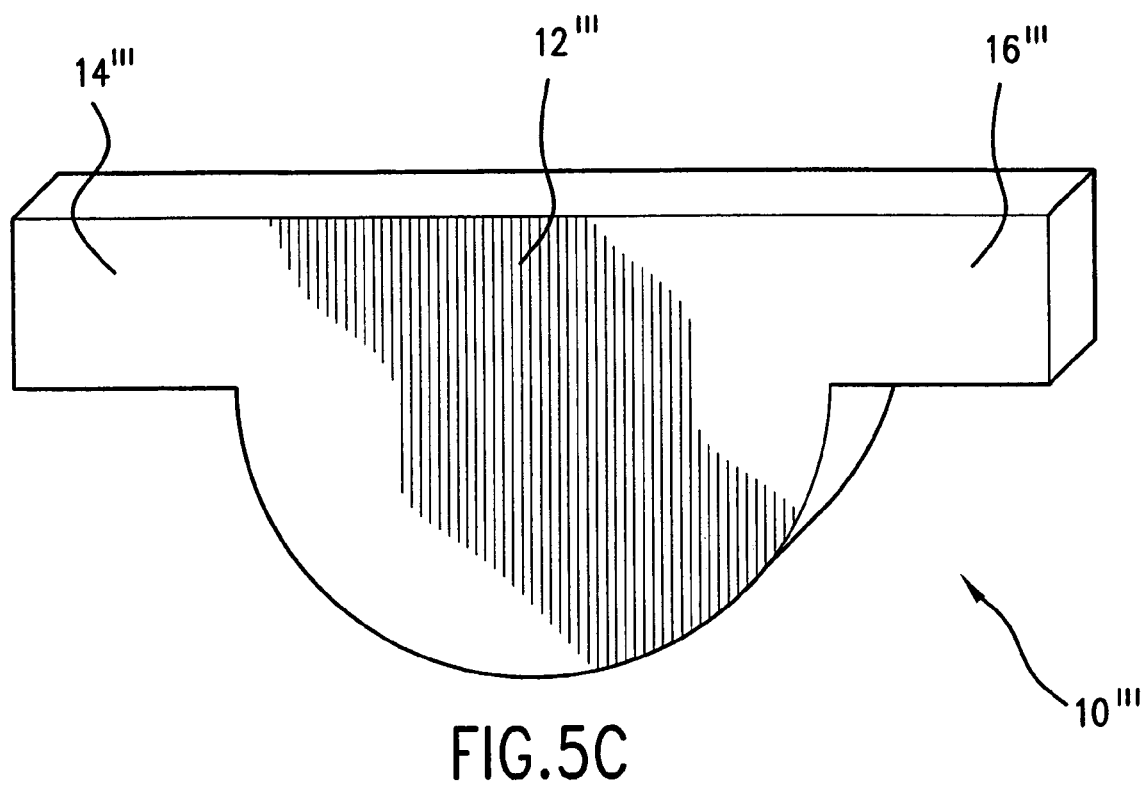

Referring to FIGS. 5a–5c, alternative embodiments of the pubovaginal support 10' are illustrated. FIG. 5a illustrates an oval-shaped support 10' in accordance with the present invention. The oval-shaped embodiment includes a body 12' and two extensions 14', 16'. The oval-shaped embodiment is similar to the preferred embodiment. However, since there is no portion of the body to roll, fold, or arrange for added bulk, the body 12' of the oval-shaped embodiment is made with increased stiffness in at least the body 12' area.

FIG. 5b illustrates a rectangular shaped support 10" in accordance with the present invention. Just as with the oval-shaped embodiment, the rectangular-shaped embodiment also has a body 12" and two extensions 14", 16". The rectangular-shaped embodiment is similar to the embodiment illustrated in FIG. 2. However, since there is no portion of the body to roll, fold, or arrange, for added bulk, the body 12" of the rectangular-shaped embodiment is made with increased stiffness in at least the body 12" area.

FIG. 5c illustrates a bow-shaped embodiment in accordance with the present invention. The bow-shaped embodiment also has a body 12''' and two extensions 14''', 16'''. The body 12''' is oblong, and bows outward on at least one side.

The bowed portion may be folded, rolled, or otherwise arranged, to provide added bulk. If however, the body of the bow-shaped embodiment is made with increased stiffness in at least the body 12''' area, no rolling, folding, or arranging is required. Instead, the body 12''' will provide support further along the length of the urethra 34, between the bladder neck 32, and the sphincter urethrae muscle 40. It will be appreciated by one skilled in the art that a variety of shapes of the support may be used to achieve the present invention. Any shape having a body for providing bulk, and extensions to bear force and hold the support 10 in the surrounding peri-urethral tissue 38 may be used to achieve the present invention.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents.

What is claimed is:

1. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein a length of the support measured across the extensions and the body portion is between 2 to 5 centimeters.

2. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein a thickness of the support is from 2 millimeters to 1 centimeter.

3. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein a width of the support is between 0.5 centimeters to 3 centimeters.

4. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein a height of the body portion of the support is between 1.0 and 6 centimeters.

5. The pubovaginal support of claim 1, wherein a thickness of the support is between 2 millimeters and 1 centimeter, and a width of the support is between 0.5 centimeters and 3 centimeters.

6. The pubovaginal support of claim 1, wherein the length of the support is about 4 centimeters.

7. The pubovaginal support of claim 2, wherein the thickness of the support is about 0.5 centimeters.

8. The pubovaginal support of claim 2 wherein the thickness of the support is about 1 centimeter.

9. The pubovaginal support of claim 3, wherein the width of the support is between 1 to 2 centimeters.

10. The pubovaginal support of claim 1, wherein the length of the body portion of the support is between 1 to 3 centimeters.

11. The pubovaginal support of claim 5, wherein the thickness is about 0.5 centimeter, the width is between 1 to 2 centimeters, and the length is about 4 centimeters.

12. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein the support deflects between 0 to 3 millimeters under 500 grams of weight applied at the center point of the body portion.

13. The pubovaginal support of claim 8, wherein the support deflects 2 to 3 millimeters under 500 grams of weight applied at the center point of the body portion.

14. A self-stabilizing pubovaginal support for treating human female urinary incontinence which is wholly implantable in the peri-urethral tissue of said female comprising:
    an elongate body portion having sufficient bulk and stiffness to lift and support the urethra and bladder neck of said female upon implantation in said peri-urethral tissue adjacent said urethra; and
    at least two extensions extending away from the body portion sized and configured for securing said support wholly within said peri-urethral tissue without ex-peri-urethral attachment and wherein the thickness of the body portion is about 1 centimeter.

15. A method of treating human female urinary incontinence for a patient having a vagina with an anterior wall, a bladder, a bladder neck, a sphincter urethrae muscle, and peri-urethral tissue, comprising:
- making an incision in the anterior wall of the vagina parallel to an area between the bladder and the sphincter urethrae muscle;
- opening the incision to provide access to the peri-urethral tissue;
- dissecting at least two pockets in the peri-urethral tissue on either side of a urethra and between the bladder and sphincter urethrae muscle;
- positioning a pubovaginal support, including a body portion and at least two extensions, underneath the urethra and the bladder neck and between the bladder and the sphincter urethrae muscle, with the at least two extensions placed in the at least two pockets, the support being wholly implanted in peri-urethral tissue without ex-peri-urethral attachment; and closing the incision.

16. The method of claim 15, wherein the step of closing the incision comprises looping incision stitches through the support.

17. The method of claim 15 further comprising, after positioning the pubovaginal support:
- securing the support with at least two sutures.

18. The method of claim 15 further comprising, after positioning the pubovaginal support: securing the support with surgical glue.

19. The method of claim 15 further comprising, after positioning the pubovaginal support:
- arranging a portion of the body of the support to provide added bulk.

20. The method of claim 15 further comprising, performed prior to making an incision in the anterior wall of the vagina:
- inserting a probe into the urethra and tapping the probe from the anterior wall of the vagina to identify the incision area.

21. The method of claim 15, wherein positioning a pubovaginal support comprises:
- manipulating the body portion of the support so that the body portion overlaps itself to form a portion of increased bulk underneath the urethra and bladder neck.

22. The method of claim 21, wherein said manipulating includes a process selected from the group consisting of folding and rolling.

23. A self-stabilizing pubovaginal support for treating human female urinary incontinence which is wholly implantable in the peri-urethral tissue of said female consisting essentially of:
- a body portion having sufficient bulk and stiffness to lift and support the urethra and bladder neck of said female upon implantation in said peri-urethral tissue adjacent said urethra; and
- at least two extensions having the same longitudinal axis extending away from the body portion sized and configured for securing said support wholly within said peri-urethral tissue without ex-peri-urethral attachment.

* * * * *